United States Patent [19]

Hahn et al.

[11] 4,286,599
[45] Sep. 1, 1981

[54] MARKING DEVICE

[75] Inventors: Douglas D. Hahn; Dennis E. Epley; Kenneth I. Granle, all of Austin, Minn.

[73] Assignee: Geo. A. Hormel & Company, Austin, Minn.

[21] Appl. No.: 2,998

[22] Filed: Jan. 12, 1979

[51] Int. Cl.³ .............................................. A61D 7/00
[52] U.S. Cl. ................................... 128/316; 81/9.22
[58] Field of Search .................. 128/316, 329 R, 253, 128/234, 235, 218 A, DIG. 1, 215, 218 G, 218 P, 218 R; 227/108; 81/9.22; 40/300

[56] References Cited

U.S. PATENT DOCUMENTS 2,593,110  4/1952  Crane et al. .......................... 128/329
3,144,867  8/1964  Trupp et al. .......................... 128/234
3,362,406  1/1968  Logsdon ........................... 128/218 R

FOREIGN PATENT DOCUMENTS 110725  5/1900  Fed. Rep. of Germany ............ 81/9.22

Primary Examiner—Robert W. Michell
Assistant Examiner—Michael H. Thaler
Attorney, Agent, or Firm—Williamson, Bains, Moore & Hansen

[57] ABSTRACT

A marking device for marking animals, such as hogs, prior to slaughter includes a handle having a housing at one end which is provided with a plurality of hollow needles arranged to define identification numbers. A pump on the housing causes ink to be dispensed through the needles as the needles penetrate the animal's skin so that the identification numbers are formed in the subcutaneous fat layer of the animal.

5 Claims, 5 Drawing Figures

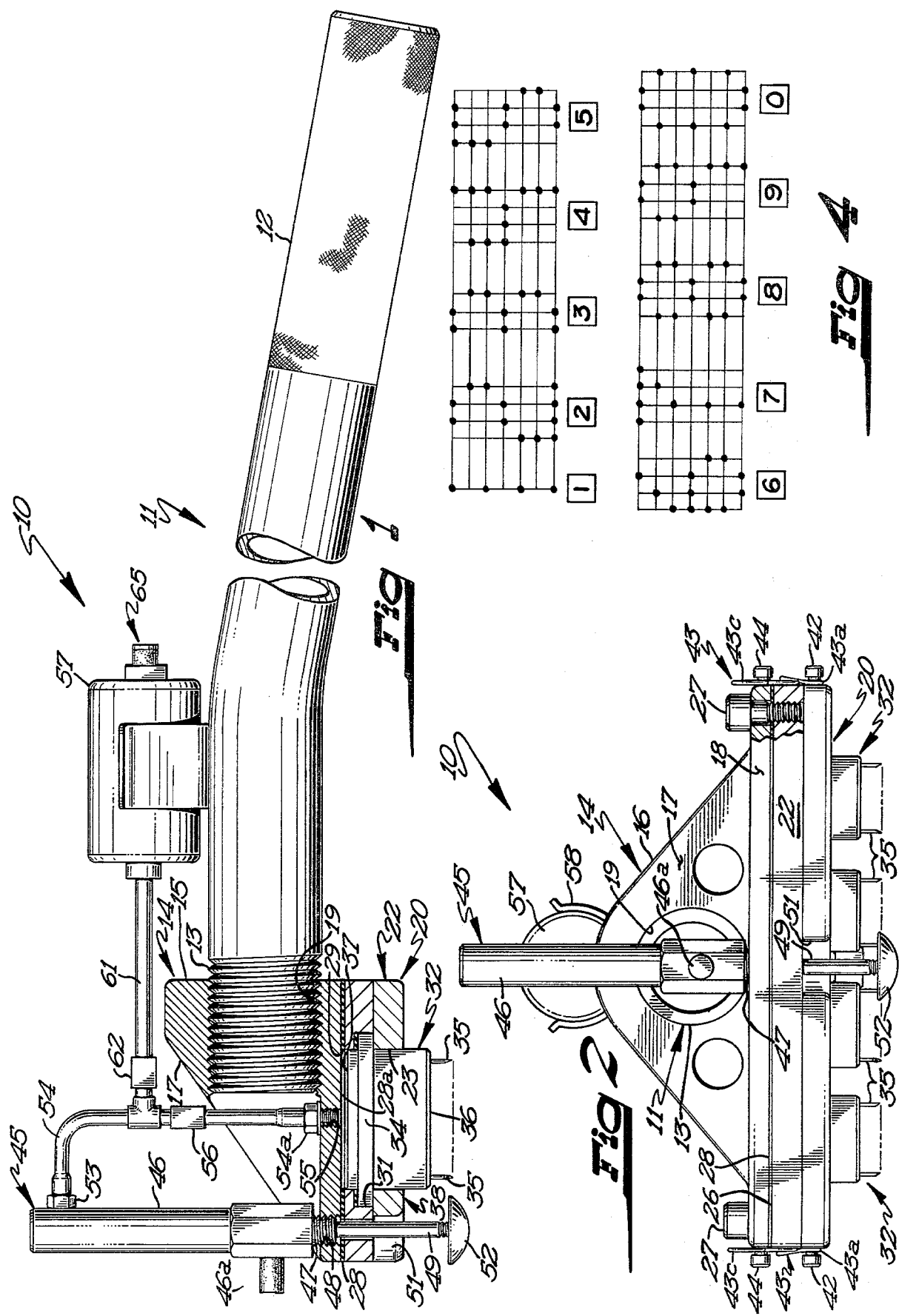

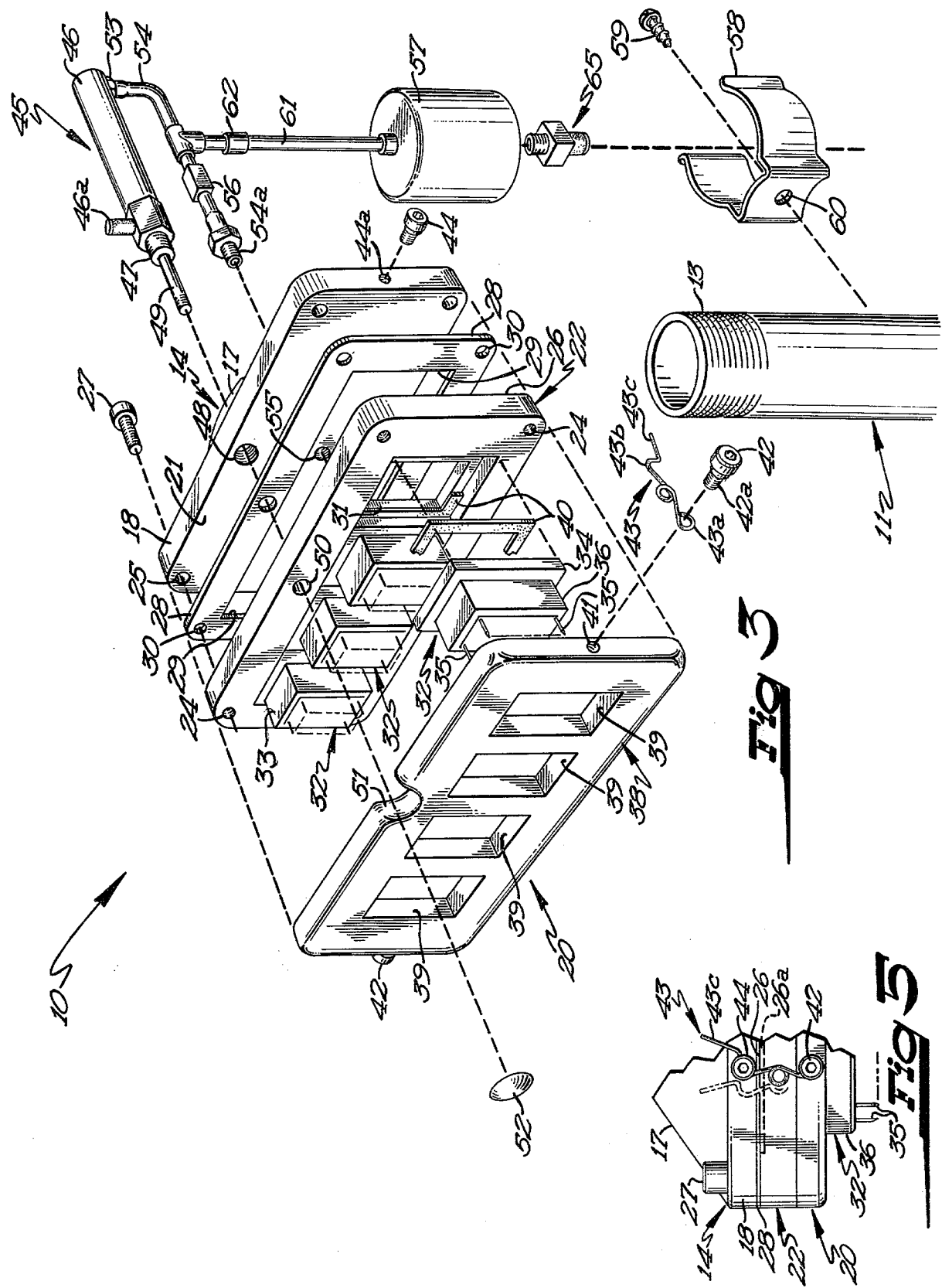

MARKING DEVICE

SUMMARY OF THE INVENTION

This invention relates to a marking device and more particularly to a marking device for tattooing numbers on an animal, such as hogs and the like.

In the meat packing industry, animals, such as hogs, are marked with identification numbers prior to slaughter. Such numbers are used to indicate the grade of the animal for evaluating the animal with respect to the buying and selling prices thereof. Heretofore, these identifying numbers have been applied to the skin of the animal prior to slaughter and these numbers remain visible and discernible, even after slaughter, dressing, scalding and singeing of the animal carcass.

However, pursuant to recent developments in the meat packing industry, slaughter animals, such as hogs and the like, are completely skinned on the kill floor immediately after evisceration. Therefore, any identifying numbers applied to the skin would be removed with the skin during the skinning operation.

It is therefore an object of this invention to provide a marking device which is operable for tattooing inked numbers in the subcutaneous fat layer of the animal prior to slaughter.

More specifically, it is an object of this invention to provide a hand-type marking device including a handle provided with a plurality of hollow needles thereon arranged to define numbers, and a pump which is operable to cause ink to be dispensed from the needles as the needles are caused to penetrate the skin of the animal to thereby tattoo to the identification numbers on the subcutaneous fat layer of the animal.

These and other objects and advantages of this invention will more fully appear from the foregoing description made in connection with the accompanying drawings, wherein like reference characters refer to the same or similar parts throughout the several views.

FIGURES OF THE DRAWINGS

FIG. 1 is a side elevational view of the novel marking device, with certain parts thereof illustrated in sections to more clearly disclose the relationship of the parts;

FIG. 2 is a front elevational view of the marking device;

FIG. 3 is an exploded perspective view of one end of the marking device; and

FIG. 4 is an elevational view of a plurality of marking units illustrating the arrangement of the needles for each unit to define a number.

FIG. 5 is a fragmentary elevational view of the marking device illustrating certain components thereof.

DESCRIPTION OF THE PREFERRED EMBODIMENT

Referring now to the drawings and more specifically to FIG. 1, it will be seen that one embodiment of the marking device, designated by the reference numeral 10, is thereshown. The marking device 10 includes an elongate, cylindrical handle 11 having one end portion thereof knurled as at 12 and having the other end portion thereof threaded as at 13. The knurled end portion 12 facilitates gripping of the handle by a user. The threaded end 13 of the handle is adapted to threadedly engage a housing 14 which may be formed of any suitable rigid material such as metal, plastic or the like. In the embodiment shown, the housing includes a substantially flat generally triangular shaped rear surface 15, a curved upper surface 16, a sloping front surface 17, and a substantially flat lower surface 21. The rear surface 15 of the housing has a threaded socket 19 therein which threadedly engages the end 13 of the handle 11.

The marking device 10 also includes a mounting assembly 20 which is secured to the flat lower surface 21 of the housing 14. The mounting assembly 20 includes a generally rectangular shaped manifold member 22 having length and width dimensions of the lower surface 21 of the housing 14. The manifold member 22 is provided with a plurality of similar rectangular openings 23, four such openings being shown in the embodiment illustrated. The manifold member 22 is also provided with threaded apertures 24 therethrough located adjacent the corners of the manifold member and which are disposed in registering relation with respect to apertures 25 in the lower surface 21 of the housing 14. The manifold member 22 has a substantially flat upper surface 26 having a generally rectangular shaped recess 26a therein. Cap screws 27 project through the openings 25 in the lower surface 21 and threadedly engage in the threaded apertures 24 to secure the manifold members to the housing 14.

A generally rectangular shaped gasket 28 is interposed between the manifold member 22, and the lower surface 21 of the housing 14. The gasket 28 has a large rectangular shaped opening 29 therein and this opening defines an area which corresponds to the area including the rectangular shaped openings 23 in the manifold member. Thus, the edges of the rectangular opening 29 in the gasket 28 will be disposed in registering relation with respect to the upper and lower edges of the rectangular openings 23 and in registering relation with the outer side edges of the outermost openings 23.

The gasket 28 is also provided with apertures 30 which are disposed in registering relation with the apertures 25 and through which the cap screws 27 project. The gasket 28 forms a seal between the peripheries of the housing 14 and the manifold member 22. The recess 26a defines an ink distribution chamber, which will be more fully described hereinbelow. It will also be seen that the rectangular openings 23 in the manifold member have a shoulder 31 defined by an enlarged portion or each opening.

A plurality of generally rectangular shaped marking units 32 are provided, each including a rectangular needle holder 33, each rectangular needle holder having a rectangular flange 34 projecting outwardly therefrom. Each needle holder has a plurality of hollow needles 35 embedded therein and extending therethrough. In this respect, it will be seen that the hollow needles project outwardly from the outer end 36 of each needle holder and each needle has its other end terminating in substantially coplanar relation with respect to the inner end 37 of the associated needle holder. Thus, the inlet ends of the needles 35 communicate with the chamber 26a. The needles in each needle holder are arranged to define indicia, preferably numbers, as illustrated in FIG. 4 of the drawings.

Each of the marking units 32 is positioned within one of the openings 23 of the manifold member so that the flange 34 of each marking unit engages the associated shoulder 31. A generally rectangular shaped gasket 40 is disposed between the manifold member 22 and the marking units 32. The gasket 40 has four openings therein to accommodate the marking units 32 and forms a fluid seal between the peripheries of the marking units and manifold member. When so positioned, the inner ends 37 of each marking unit holder 33 is positioned closely adjacent the opposite surface 26 of the manifold member.

Means are provided for retaining the marking unit 32 in the openings 23 of the manifold member and this means includes a generally rectangular shaped retainer member 38. The retainer member 38 also has length and width dimensions corresponding to the length and width dimensions of the manifold member 22. The retainer member also has rectangular shaped openings 39 which correspond in size, configuration and position to the rectangular openings 23 in the manifold member 22.

Means are provided for securing the retainer member 38 to the manifold member 22 in a manner to permit quick removal and reattachment of the retainer member to the manifold member. The retainer member 38 has a pair of apertures 41 therein, each being located in one end thereof. These apertures 41 are threaded for receiving the threaded end portion 42a of a bolt 42. The looped end 43a of the spring 43 receives the shank of the bolt 42 therethrough to secure the spring to the retainer member 38. The spring 43 is also provided with a loop portion 43b adjacent its other end. This loop portion 43b is adapted to frictionally engage a bolt 44 which threadedly engages a threaded aperture 44 in the end of the housing 14. The spring 43 is also provided with a finger engagement portion 43c to facilitate movement of the spring into and out of the bolt 44.

It will be seen that when the looped end 43b engages the shank of the bolt 44, the retainer member will clamp the marking unit and manifold member against the housing 14. When it is desirable to change the marking unit for different indicia, it is merely necessary to disengage the springs 43 from frictional engaging relation with respect to the bolts 44 to remove the retaining member and thereafter replace the marking units.

The marking device 10 is also provided with a pump 45 including an elongate cylinder or chamber structure 46 having a reduced threaded end portion 47 which threadedly engages in a threaded aperture 48 in the housing 14 adjacent the front pump thereof. The pump 45 also includes an elongate plunger 49 which is moveable in the pump cylinder 46 and which projects therefrom through an opening 50 in the manifold member 22 and through a recess 51 in the retainer member 38. An actuator button 52 is secured to the outer end of the plunger 49, the actuator button having a convex, lower surface. The pump cylinder 46 has an intake opening therein provided with an intake filter 46a. Although not shown in the drawing, the pump is provided with a spring which serves to urge the plunger outwardly. Thus, retractive movement of the plunger into the pump cylinder is against the bias of the spring. It will be noted that when the plunger is in an outward or extended position, as best seen in FIG. 1, the lower convex surface of the actuator button 52 extends beyond the outlet ends of the needles 35 of the marking units 32.

The pump cylinder 46 is provided with an outlet port 53 which is connected in communicating relation to one end of a conduit 54, the other end of the conduit 54 being connected with a threaded opening or port 55 in the housing 14 by means of threaded connector 54a. The port 55 communicates with the chamber defined by the gasket 28, the chamber communicating with the inlet ends of the hollow needles 35. A check valve 56 is interposed in flow controlling relation with respect to the conduit 54 and prevents the return of air into the pump cylinder 46.

The marking device 10 also includes a reservoir container 57 for containing a supply of ink, the reservoir container 57 being secured to the handle 11 by a bracket 58. The bracket 58 has an opening therethrough for accommodating a screw 59 which engages in a threaded opening in the handle 11. An elongate conduit 61 has one end thereof connected in communicating relation with the reservoir container 57 and has the other end thereof connected in communicating relation with the conduit 54. A check valve 62 is interposed in flow controlling relation with respect to the conduit 61 and serves to prevent return of ink into the reservoir container 57. Another check valve 65 is inserted into reservoir 57 and serves to equalize the pressure on the expanding air chamber. The check valve 65 in reservoir 57 as ink is drawn also prevents the loss of ink when ink is drawn from the reservoir along with air from the exterior.

In use, an operator will grip the handle, and will then apply the housing against an animal to be marked. When so applied, the actuator button 52 will engage the surface of the animal thereby causing the pump plunger 49 to be urged into the pump cylinder. As the marking device is pressed against the skin of the animal, the needles 35 of the marking units will penetrate the skin and will enter the subcutaneous fat layer located directly below the skin. The plunger will cause ink flow from the pump 45 through the conduit 54 and into the chamber 26a defined by the manifold 22. Ink will flow through the hollow needles and a tattooed pattern will be formed in the subcutaneous fat layer of the animal. In hogs, the subcutaneous fat layer is of substantial thickness. The marking device can then be withdrawn and will be in condition for the next animal. In the event that a separate number is applied to each animal, the operator will replace one of the marking units 32 by quickly removing the spring loops 43b from bolts 44, removing the retainer member 38 and thereafter removing and replacing one of the marking units 32. The fastener elements may then be replaced by the operator and the marking device applied to the next animal to be marked. It is pointed out that marking ink may be applied directly to the needles 35 by means of a brush. When used in this manner no reservoir container is needed inclusive of check valves 56 and 62, and conduit 61.

Referring to FIG. 4, it will be seen that the hollow needles 35 of each marking unit are preferably arranged to define numbers although other indicia, such as letters, may be used. It has been found that even when the skin of the animal is removed, the tattooed numbers will be plainly visible and discernible on animals marked with the marking device 10 since these numbers have been effectively tattooed in the fat layer of the animal. Thus, the marking device 10 is especially adapted in tattooing animals, such as hogs, wherein the skin is removed immediately after slaughter.

From the foregoing description, it will be seen that I have provided a novel marking device which is not only of simple and inexpensive construction, but one which functions in a more efficient manner than any heretofore known comparable device.

It is anticipated that various changes can be made in the size, shape and construction of the Marking Device disclosed herein without departing from the spirit and scope of the invention as defined in the following claims.

What is claimed is:

1. A marking device for applying marking indicia to the subcutaneous area of animals prior to slaughter, comprising:

an elongate handle;

a housing secured to one end of said handle;

a needle holder assembly secured to said housing;

a marking unit including a needle support, a plurality of hollow marking needles on said support and being arranged to define a number, said marking unit being mounted on said housing by said holder assembly;

means defining a chamber in said housing communicating with said needles;

ink dispensing means comprising a pump cylinder on said housing containing marking ink and communicating with said needles, a plunger being extensible and retractable in said pump cylinder and projecting outwardly of the latter, said plunger when in the extended position having its outer end extending beyond the needles, said plunger when moved to the retracted position causing ink to flow from the pump housing into and through the needles, whereby when the marking device is applied to the skin of an animal, such as a hog, the actuator will first engage to the animal's skin just prior to penetration of the needles through the skin whereby ink will be dispensed in a predetermined pattern through the needles into the subcutaneous fat layer of the animal.

2. The marking device as defined in claim 1 and a plurality of additional marking units each including a needle support and a plurality of hollow needles arranged to define a number, said additional marking units being disposed in side by side relation and being secured to said housing by said holder assembly.

3. The marking device as defined in claim 2 wherein said holder assembly includes a manifold member having a plurality of openings therein for receiving said marking units, said manifold member cooperating with said housing to define said chamber.

4. The marking device as defined in claim 3 wherein said holder assembly includes a retainer member releasably secured to said manifold member for securing the marking units to the latter.

5. The marking device as defined in claim 1 and a reservoir structure on said handle containing said supply of ink, means interconnecting said reservoir structure in fluid communication with said chamber and said pump cylinder.

* * * * *